(12) United States Patent
Kaneko et al.

(10) Patent No.: US 9,745,403 B2
(45) Date of Patent: Aug. 29, 2017

(54) POLYMER RAW MATERIAL AND POLYMER MATERIAL

(71) Applicant: JAPAN ADVANCED INSTITUTE OF SCIENCE AND TECHNOLOGY, Ishikawa (JP)

(72) Inventors: Tatsuo Kaneko, Nomi (JP); Akio Miyazato, Nomi (JP); Seiji Tateyama, Nomi (JP); Phruetchika Suvannasara, Nomi (JP); Yuuki Oka, Nomi (JP)

(73) Assignee: JAPAN SCIENCE AND TECHNOLOGY AGENCY, Kawaguchi-Shi, Saitama (JP)

( * ) Notice: Subject to any disclaimer, the term of this patent is extended or adjusted under 35 U.S.C. 154(b) by 66 days.

(21) Appl. No.: 14/357,954

(22) PCT Filed: Nov. 13, 2012

(86) PCT No.: PCT/JP2012/079354
§ 371 (c)(1),
(2) Date: May 13, 2014

(87) PCT Pub. No.: WO2013/073519
PCT Pub. Date: May 23, 2013

(65) Prior Publication Data
US 2014/0323679 A1 Oct. 30, 2014

(30) Foreign Application Priority Data
Nov. 17, 2011 (JP) ................. 2011-252006

(51) Int. Cl.
| | | |
|---|---|---|
| C08G 18/38 | (2006.01) |
| C08G 18/32 | (2006.01) |
| C08G 69/26 | (2006.01) |
| C08G 73/14 | (2006.01) |
| B01J 19/12 | (2006.01) |
| B01J 19/08 | (2006.01) |
| C08G 18/34 | (2006.01) |
| C08G 73/10 | (2006.01) |
| C08J 11/14 | (2006.01) |
| C08J 11/10 | (2006.01) |
| C08G 69/28 | (2006.01) |
| C08G 69/32 | (2006.01) |
| C08G 18/75 | (2006.01) |
| C07C 229/46 | (2006.01) |
| C08G 18/73 | (2006.01) |
| C08G 18/76 | (2006.01) |
| C08G 18/10 | (2006.01) |

(52) U.S. Cl.
CPC ........ *C08G 18/3821* (2013.01); *B01J 19/081* (2013.01); *B01J 19/123* (2013.01); *C07C 229/46* (2013.01); *C08G 18/10* (2013.01); *C08G 18/3234* (2013.01); *C08G 18/3243* (2013.01); *C08G 18/34* (2013.01); *C08G 18/3825* (2013.01); *C08G 18/3857* (2013.01); *C08G 18/73* (2013.01); *C08G 18/75* (2013.01); *C08G 18/7642* (2013.01); *C08G 69/26* (2013.01); *C08G 69/28* (2013.01); *C08G 69/32* (2013.01); *C08G 73/1003* (2013.01); *C08G 73/1007* (2013.01); *C08G 73/1067* (2013.01); *C08G 73/1075* (2013.01); *C08G 73/1078* (2013.01); *C08G 73/14* (2013.01); *C08J 11/10* (2013.01); *C08J 11/14* (2013.01); *C07C 2101/04* (2013.01); *C08J 2377/06* (2013.01); *C08J 2377/10* (2013.01)

(58) Field of Classification Search
CPC ..... B01J 19/123; B01J 19/081; C07C 229/46; C07C 2101/04; C08J 2377/10; C08J 2377/06; C08J 11/10; C08J 11/14; C08G 18/34; C08G 18/3821; C08G 18/3825; C08G 18/3857; C08G 18/75; C08G 18/73; C08G 18/7642; C08G 69/26; C08G 69/28; C08G 69/32; C08G 73/14; C08G 73/1078; C08G 73/1067; C08G 73/1007; C08G 73/1003; C08G 73/1075; C08G 18/3234; C08G 18/3243
See application file for complete search history.

(56) References Cited

U.S. PATENT DOCUMENTS 6,811,833 B2 * 11/2004 Nishikawa ............. C07C 62/34
428/1.1
2003/0102458 A1 6/2003 Nishikawa et al.

FOREIGN PATENT DOCUMENTS

| JP | H02-028208 A | 1/1990 |
| JP | 2006-137820 A | 6/2006 |

OTHER PUBLICATIONS

PCT, "International Search Report for International Application No. PCT/JP2012/079354".

(Continued)

*Primary Examiner* — Rabon Sergent
(74) *Attorney, Agent, or Firm* — Manabu Kanesaka

(57) ABSTRACT

To provide a polymer material having properties that allow the polymer material to replace a polyimide and a polyamide synthesized from a petroleum raw material, said polymer material being synthesized from a raw material derived from natural molecules. [Solution] This polymer material is obtained by polymerizing a polymer raw material comprising a dimer of 4-amino cinnamic acid or a dimer of a 4-amino cinnamic acid derivative, which are natural molecules, wherein the carboxyl group is protected by an alkyl chain. The TGA curve of a polyamide acid (PAA-1) and a polyimide (PI-1) according to the present invention is shown in FIG. 5.

11 Claims, 9 Drawing Sheets

(56) References Cited

OTHER PUBLICATIONS

Fritz M. Kreuzaler und Christoph Peterh, Technische Hochschule Aachen; Apr. 2009Y; "Rekombinante Biosynthese amino-substituierter Phenylpropanoide in *E. coli*".

I. Taenaesescu und F. Hodosan, Revue de Chime; Tome I, 1956Y, No. 2; "Die Photodimer1sation der Nitrozimtsaeuren und der Nitrochalkone".

\* cited by examiner

POLYMER RAW MATERIAL AND POLYMER MATERIAL

RELATED APPLICATIONS

The present application is National Phase of International Application No. PCT/JP2012/079354 filed Nov. 13, 2012, and claims priority from Japanese Application No. 2011-252006, filed Nov. 17, 2011.

TECHNICAL FIELD

The present invention relates to a naturally-derived polymer raw material and a polymer material comprising the polymer raw material.

BACKGROUND ART

Polymer materials such as polyimide and polyamide are high-performance plastics which are used as high-performance industrial products in fields of electrotechnology, electronics, space technology, etc., and needs for them are extremely high. For a body, interior parts and electric components of a vehicle, not a little polyimide and polyamide resins are used, for example.

Conventionally, almost all polyimide and polyamide resins have been synthesized from petroleum raw materials and obtained only from petroleum resources. Thus, the reality is that the problems on exhaustion of the petroleum resources and the like are not addressed, and the rising demand for these polymer materials to be synthesized from petroleum raw materials contradicts low carbonization.

On the other hand, bioplastics as polymer materials using naturally-derived raw materials belong to the matter system expected to immobilize carbon dioxide for long periods unlike biofuels or the like, and their actual utilization may considerably contribute to the low carbonization, but cost growth is a big problem. From different viewpoints, even in a case of using a high-cost biomolecule, any high value-added material like a super engineering plastic can obtain sufficient cost-benefit performance, and thus it can potentially be spread throughout society.

From such a situation, manufacturing methods of polyamide resins using naturally-derived polymer raw materials have been recently studied. In addition, industrial materials using compounds which are the same as or close to naturally-derived polymer raw materials are known in the literatures.

PRIOR ART DOCUMENT

Patent Document

Patent Document 1 discloses a manufacturing method of a polyamide resin using a diamine and a dicarboxylic acid derived from a compound on a metabolic pathway of lysine in a microorganism. Patent Document 1 describes that a bend elastic constant achieved 3-5 GPa and a glassy-transition temperature TG achieved 120-180° C. in a polyamide resin. Patent Document 2 describes an optical member having a four-membered cyclic compound.

Literature 1 describes an aromatic alcohol compound substituted with an amino group. Literature 2 describes a polymer raw material composed of a dimer of amino cinnamic acid.

Patent Document 1: JP2006-137820 A1
Patent Document 2: JP2003-160540 A1

Literature 1: Fritz M. Kreuzaler und Christoph Peterh, Technische Hochschule Aachen; April 2009Y; "Rekombinante Biosynthese amino-substituierter Phenylpropanoidein E. coli"

Literature 2: I. TAENAESESCU und F. HODOSAN, REVUE DE CHIMIE; Tome I, 1956Y, No 2; "DIE PHOTODIMERISATION DER NITROZIMTSAEUREN UND DER NITROCHALKONE"

BRIEF SUMMARY OF THE INVENTION

Problems the Invention Intends to Solve

However, synthesis of high-performance polyimide and polyamide from a biological resource material is associated with a lot of difficulties. This is because a toxicity of an aromatic diamine as a raw material for polyimide and polyamide is too high to produce from an organism.

Moreover, in actual conditions, when comparing bioplastics using a biological resource material as a raw material with a polyimide resin or a polyamide resin synthesized from a petroleum raw material, the heat resistance performance of the bioplastics is not necessarily sufficient. For example, a heat-resistant temperature of a conventional bioplastic is only about 305 deg C. at most. Because of the background that conventional bioplastics were developed as biodegradable plastics, their performances have not been adequately pursued. The reason for that is because polyester-based plastics with low heat resistance performance has been used so as to enable decomposition.

The present invention was proposed in light of such conventional circumstances, the purpose is to provide an organism-derived polymer raw material capable of synthesizing a biopolymer having performances which can supersede those of polyimide and polyamide synthesized from petroleum raw materials, and provide a naturally-derived polymer material having performances which can supersede those of polyimide and polyamide synthesized from petroleum raw materials by using the polymer raw material.

Means for Solving the Problems

The polymer raw material of the present invention is characterized in that it comprises a dimer of 4-amino cinnamic acid or 4-amino cinnamic acid derivative, can be polymerized by protecting a carboxyl group with an alkyl chain, and has a structure represented by Formula 1.

[Formula 1]

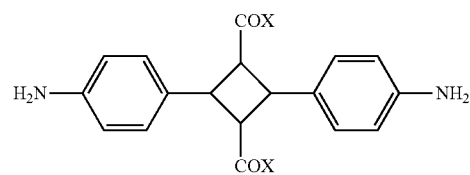

wherein: x is any one of —OR, —SR and —NHR; and R is any one of alkyl group, alkenyl group, aryl group and oxyalkylene group.

As shown in Formula 1, the polymer raw material of the present invention comprises the dimer of 4-amino cinnamic acid or 4-amino cinnamic acid derivative as a basic structure and has amino groups through phenyl groups on both ends of the four-membered ring. That is, the polymer raw material of the present invention has a structure equal to that of aromatic diamine which may be a raw material of polyimide and polyamide.

As shown in Formula 1, the polymer raw material of the present invention has two carboxyl groups derived from the dimer of 4-amino cinnamic acid or 4-amino cinnamic acid derivative, wherein these carboxyl groups should be protected by any protecting group so as not to react with the amino groups contained in the polymer raw material. As a protectant for forming the protecting group, any known protectants capable of protecting the carboxyl group can be used. The protection is carried out, for example by esterification, thioesterification and amidation, etc. Consequently, in Formula 1, X is, for example —OR, —SR, —NHR. Herein, R is any of an alkyl group, an alkenyl group, an aryl group and an oxyalkylene group.

When a polymer material such as polyimide and polyamide is synthesized, the polymer raw material of the present invention can be used as a naturally-derived raw material monomer, thereby a high-performance polymer material, particularly a polymer material having an extremely-high heat resistance can be provided.

The polymer material of the present invention is characterized in that it is constructed by polymerizing the polymer raw material, wherein its main chain has a structure which comprises any of an imide bond, an amide bond, an urea bond, or the amide bond and the imide bond and is represented by Formula 2.

[Formula 2]

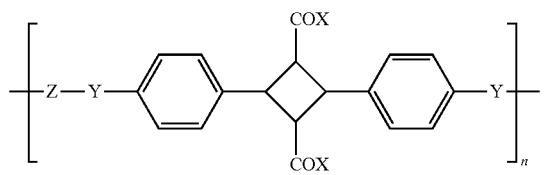

wherein: x is any one of —OR, —SR and —NHR; R is any one of alkyl group, alkenyl group, aryl group and oxyalkylene group; Y is any one of imide bond, amide bond, urea bond and amide and imide bond; Z is an organic link; and n is a positive integer.

The polymer material of the present invention is characterized in that it comprises the dimer of 4-amino cinnamic acid or 4-amino cinnamic acid derivative and is constructed by polymerizing the polymer raw material having the carboxyl group being protected with the alkyl chain, wherein its main chain has a structure which comprises any of an imide bond, an amide bond, an urea bond, or the amide bond and the imide bond and is represented by Formula 3.

[Formula 3]

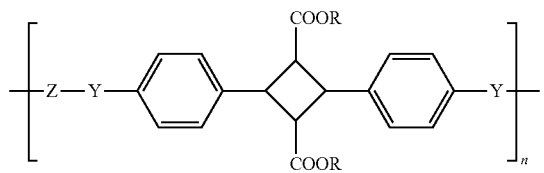

wherein: R is any one of alkyl group, alkenyl group, aryl group and oxyalkylene group; Y is any one of imide bond, amide bond, urea bond and amide and imide bond; Z is an organic link; and n is a positive integer.

More specifically, the polymer material of the present invention is characterized in that it has a structure represented by any one of Formula 4 to Formula 10.

The polymer material of the present invention is characterized in that it is a polyamide having a structure represented by Formula 4.

[Formula 4]

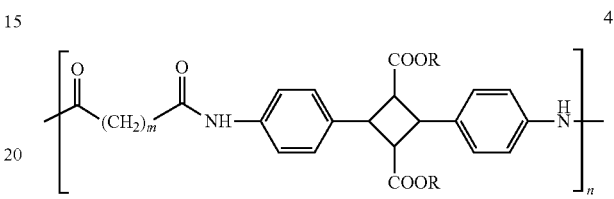

wherein: R is any one of alkyl group, alkenyl group, aryl group and oxyalkylene group; n is a positive integer; and m is a positive integer.

The polymer material of the present invention is characterized in that it is a polyamide having a structure represented by Formula 5.

[Formula 5]

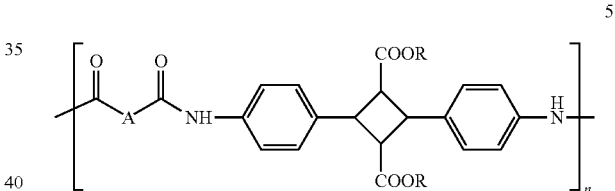

wherein: R is any one of alkyl group, alkenyl group, aryl group and oxyalkylene group; A represents an aromatic ring or a alicycle; and n is a positive integer.

The polymer material of the present invention is characterized in that its precursor is a polyamic acid having a structure represented by Formula 6.

[Formula 6]

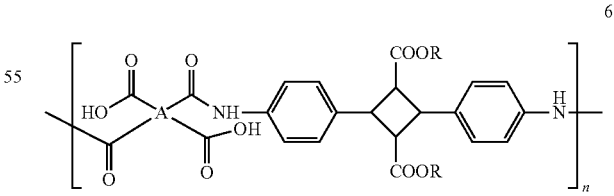

wherein: R is any one of alkyl group, alkenyl group, aryl group and oxyalkylene group; A represents an aromatic ring or a alicycle; and n is a positive integer.

The polymer material of the present invention is characterized in that it is a polyimide having a structure represented by Formula 7.

[Formula 7]

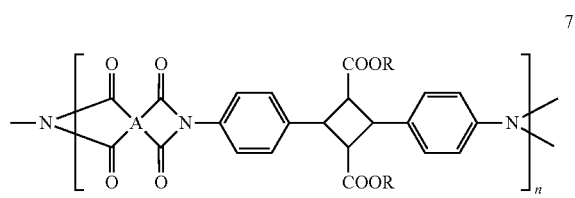

wherein: R is any one of alkyl group, alkenyl group, aryl group and oxyalkylene group; A represents an aromatic ring or a alicycle; and n is a positive integer.

The polymer material of the present invention is characterized in that it is a polyurea having a structure represented by Formula 8.

[Formula 8]

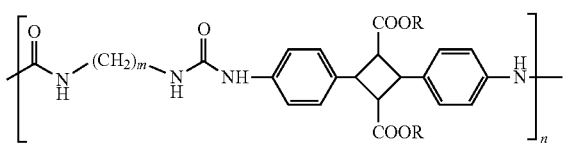

wherein: R is any one of alkyl group, alkenyl group, aryl group and oxyalkylene group; n is a positive integer; and m is a positive integer.

The polymer material of the present invention is characterized in that it is a polyurea having a structure represented by Formula 9.

[Formula 9]

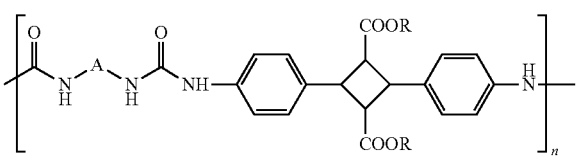

wherein: R is any one of alkyl group, alkenyl group, aryl group and oxyalkylenc group; A represents an aromatic ring or a alicycle; and n is a positive integer.

The polymer material of the present invention is characterized in that it is a polyimide having a structure represented by Formula 10.

[Formula 10]

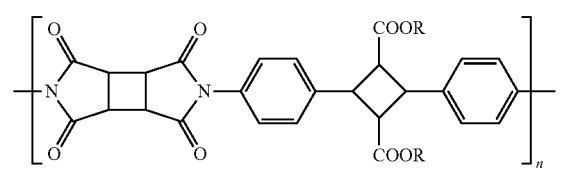

wherein: R is any one of alkyl group, alkenyl group, aryl group and oxyalkylene group; and n is a positive integer.

The polymer material of the present invention is characterized in that it comprises a biomass as a raw material.

A manufacturing method of the polymer raw material of the present invention is for synthesizing the polymer raw material which can be polymerized by protecting the carboxyl group with the alkyl chain, characterized in that the method comprises a step that an amino group is converted into hydrochloride in the 4-amino cinnamic acid or 4-amino cinnamic acid derivative, a step that dimerization reaction is conducted by ultraviolet irradiation, and a step that esterification, thioesterification or amidation was carried out by catalysis.

The manufacturing method of the polymer material of the present invention is characterized in that the polymer raw material obtained by the manufacturing method of the polymer material is converted into the polymer material by reacting its amino group to form any of an imide bond, an amide bond, an urea bond, or the amide bond and the imide bond.

A recycle method of the polymer material of the present invention is characterized in that the polymer material obtained by the manufacturing method of the polymer material is restored to the polymer raw material by any method of ultraviolet irradiation, hydrolysis using an acid after ultraviolet irradiation, hydrolysis using an acid, and ultraviolet irradiation after hydrolysis using an acid.

The polymer raw material of the present invention is synthesized by photodimerizing the dimer of 4-amino cinnamic acid or 4-amino cinnamic acid derivative which are naturally-occurring molecules, and the polymer raw material is reacted with, for example, a cyclobutanetetracarboxylic acid dianhydride which is a comonomer derived form a naturally-occurring molecule to obtain a polymer material (bioplastic) such as polyimide and polyamide. The polymer material (bioplastic) of the present invention has more than 300° C. of heat-resistant temperature and shows a heat resistance performance equal to those of known polyimide and polyamide synthesized from a petroleum raw material.

Effects of the Invention

According to the present invention, a high-performance plastic which can be utilized for electric components of a vehicle, electric and electronic fields, applications of heat-generating components such as a heater, etc. can be synthesized from a raw material derived from naturally-occurring molecule. Consequently, the plastic can supersede known polyimide and polyamide synthesized from petroleum raw materials, and low carbonization by carbon stock in the plastic can be realized. Furthermore, the polymer material of the present invention can be expected to be applied as a environmentally-compatible plastic reinforcement.

MODE FOR CARRYING OUT THE INVENTION

Figure 1:
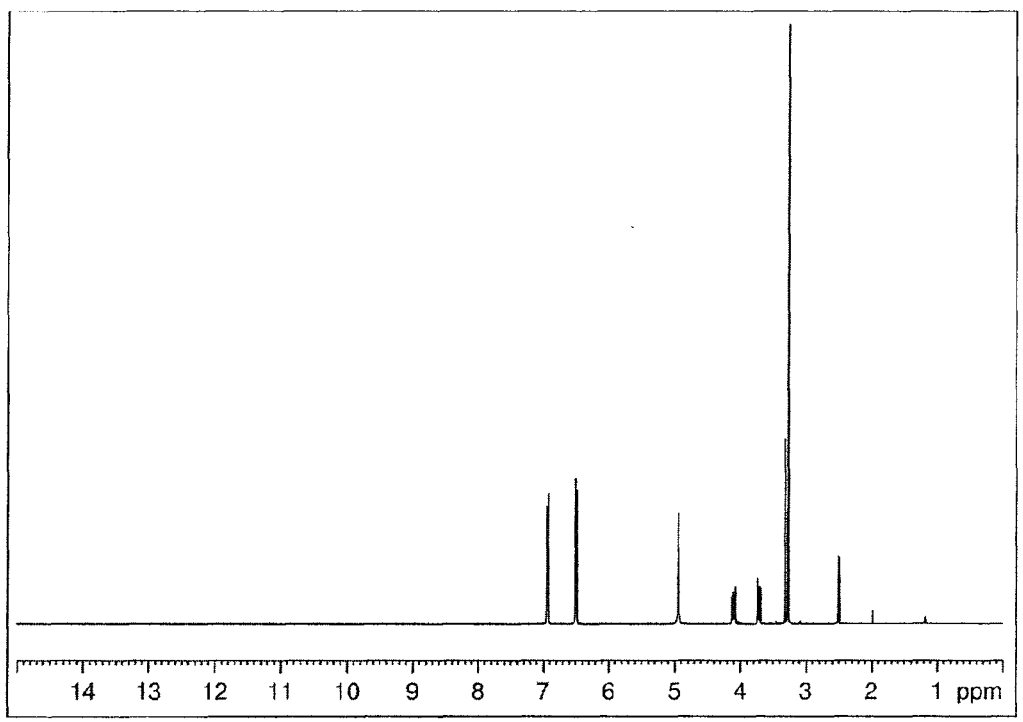
FIG. 1 is NMR spectrum of dimethyl 4,4'-diaminotruxillate (DATXA-DM) according to the present invention.

Hereinafter, the manufacturing method of the polymer raw material and the polymer material to which the present invention is applied will be detailed. Herein, its synthetic pathway is shown in the following reaction Formula 11 by taking a case that the carboxyl group is protected through esterification for example.

[Formula 11]

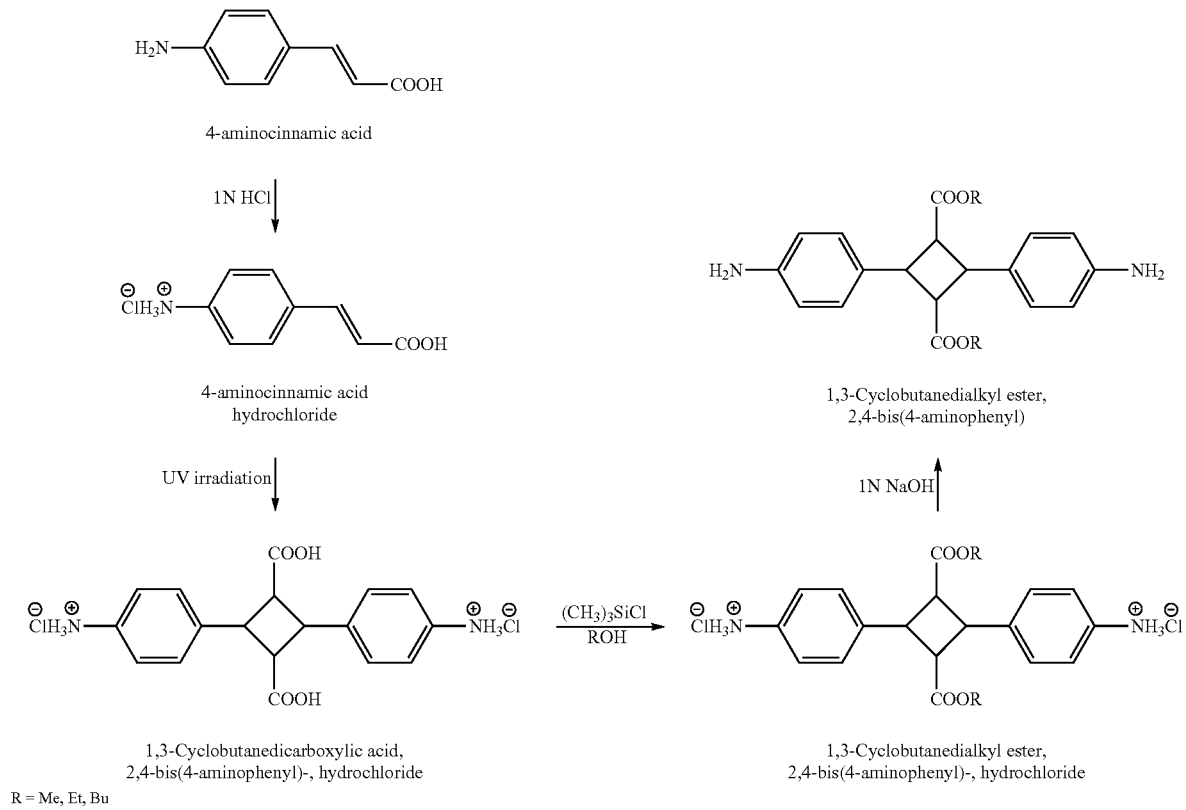

In the reaction method shown in the above reaction Formula 11, 4-amino cinnamic acid is initially activated by hydrochloric acid to hydrochlorinate an amino group of the 4-amino cinnamic acid. Subsequently, it was irradiated with ultraviolet ray for dimerization reaction. Furthermore, ROH was activated by $(CH_3)_3SiCl$ as a catalyst to esterify the carboxyl group. Herein, if RSH is used instead of ROH in esterification, it is thioesterified. In addition, if an amine is reacted instead of ROH, it is amidated. Finally, an alkali was activated to withdraw HCl, resulting in a 2,4-bis(4-aminophenyl)-1,3-cyclobutanedialkyl ester. The alkali is, for example, sodium hydroxide.

Subsequently, the polymer raw material obtained by the manufacturing method of the polymer raw material is converted into a polymer material by reacting its amino group to form any of an imide bond, an amide bond, an urea bond, or the imide bond and the amide bond. More specifically, the polymer material of the present invention has a structure represented by any of Formula 4 to Formula 10. Particularly, the polyimide represented by Formula 10 and synthesized by reacting the polymer raw material with the a cyclobutanetetracarboxylic acid dianhydride (CBDA: a dimer dianhydride of fumaric acid) which is a comonomer derived form a naturally-occurring molecule, is a polymer material which shows a high heat resistance (heat-resistant temperature: 300° C. or higher) and can contribute to low carbonization as a bioplastic.

A manufacturing method of the polyimide represented by Formula 10, which is a polymer material according to the present invention, will be detailed. The synthetic pathway for the polyimide of the present invention is shown in the following reaction Formula 12.

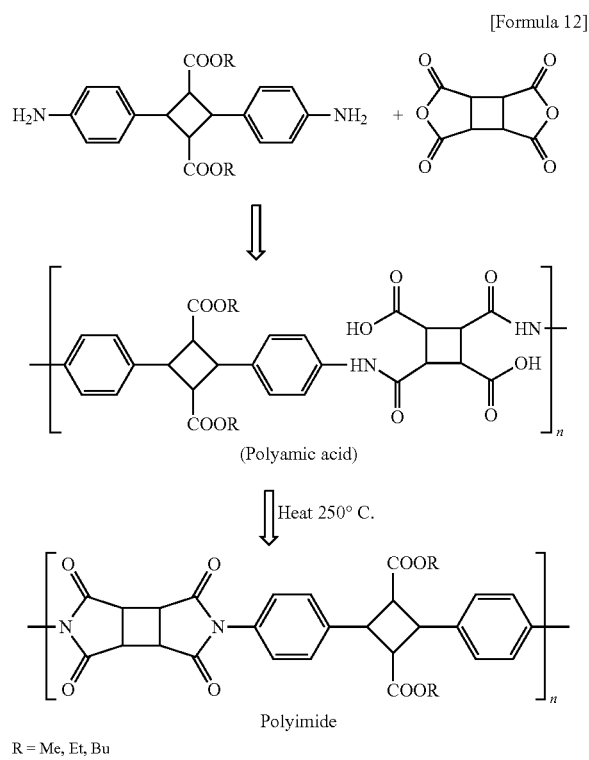

(Polyamic acid)

Heat 250° C.

Polyimide

R = Me, Et, Bu

In the reaction method shown in the reaction Formula 12, the polymer material of the present invention (2,4-bis(4-aminophenyl)-1,3-dialkyl cyclobutanedicarboxylate) is initially reacted with an acid dianhydride (cyclobutanetetracarboxylic acid dianhydride: CBDA) to synthesize a polyamide acid.

The reaction is preferably carried out, for example, in a solvent with high boiling point of 100° C. or higher. In this case, an aprotonic amide solvent is preferably used as a solvent, and for example N-methyl-2-pyrrolidinone (NMP), N,N-dimethylacetamide (DMAc), etc. are preferable.

In the reaction, after the temperature is gradually raised from room temperature to the boiling point, the reaction should be carried out for a predetermined time. The reaction time can be arbitrarily set. Additionally, in the reaction, a temperature of the raw material can be arbitrarily set. In the reaction, the concentration of the raw material is preferably 0.6 M or higher.

After synthesis of the polyamide acid, it is dehydrated by heating e.g. 250° C. or higher, thereby a polyimide represented by Formula 10 can be obtained. The polyamide acid has a high transparency and shows transmittance of approximately 100% at a wide range of wavelength. Thereby, a transparency of the polyimide obtained from the polyamide acid is also high.

In the reaction, a diisocyanate, an epoxy compound, an aryl compound having unsaturated bonds on its both ends, a dicarboxylic acid or the like is used instead of the acid dianhydride (cyclobutanetetracarboxylic acid dianhydride: CBDA), thereby a polyurea, polyamide and other various polymer materials can be synthesized. In addition, the reaction can be terminated in a state of the polyamide acid. Furthermore, if a polymer raw material having a carboxyl group and acid anhydride in one molecule like a trimellitic acid anhydride is used instead of the acid dianhydride, an polyamideimide can be synthesized.

As described above, a polymer material (biopolymer) with heat-resistant temperature of 350° C. or higher can be achieved by using the polymer raw material of the present invention. Herein, the heat-resistant temperature refers to a 10% decomposition temperature. The biopolymer obtained by the present invention can be utilized for vehicles, electric and electronic fields, applications of heat-generating components such as a heater, etc., and can supersede components using polyimide synthesized from a petroleum raw material. In addition, the polymer material synthesized using the polymer raw material of the present invention is a biopolymer comprising a naturally-occurring molecule as a raw material and may be considerably useful in the process of low carbonization.

EXAMPLES

Hereinafter, specific examples of the present invention will be detailed on the basis of the results of the experiments.

Synthesis of dimethyl 4,4'-diaminotruxillate

The synthetic pathway of dimethyl 4,4'-diaminotruxillate according to the present invention is shown in the following reaction Formula 13.

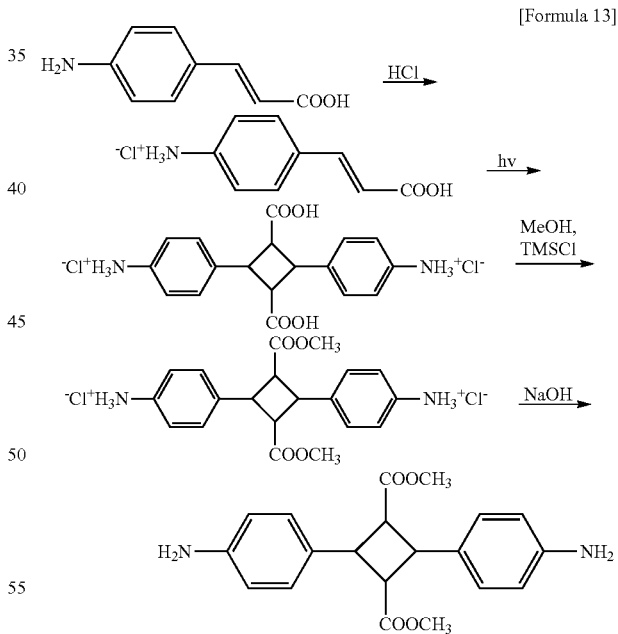

The dimethyl 4,4'-diaminotruxillate (DATXA-DM) according to the present invention can be obtained by the synthesis shown in reaction Formula 13. First, the 4-amino cinnamic acid (4-ACA) (16.3 g, 0.10 mol) and acetone (350 ml) were added to an eggplant flask and dissolved, to which 12 N of HCl (10 ml, 0.12 mol) was then slowly dripped. A generated 4-amino cinnamic acid hydrochloride (4-ACA-HCl) was collected by suction filtration, dried in a desiccator, and the 4-ACA-HCl (1.0 g, 5.0 m mol) was put in a flask, to which 20 ml of hexane was added, UV-irradiated (λ=250-450 nm) for 25 hours to obtain a 4,4'-diaminotruxillate hydrochloride (DATXA-HCl).

The same procedure was repeated, and the obtained DATXA-HCl (7.68 g, 0.019 mol), methanol (31.2 ml, 0.77 mol) and trimethylchlorosilane (9.8 ml, 0.77 mol) were put in a nitrogen-substituted flask and reacted for 42 hours for esterification. This product (3.32 g, 7.77 mmol) was put in a flask, to which 50 ml of distilled water was added and dissolved, to which 1 N of NaOH (16.2 ml) was then added for neutralization. Subsequently, ethyl acetate (280 ml) was added, and the neutralized product was dissolved and extracted using a separatory funnel to obtain a yellow powdery dimethyl 4,4'-diaminotruxillate (DATXA-DM).

NMR spectrum of the obtained dimethyl 4,4'-diaminotruxillate (DATXA-DM) is shown in FIG. 1. Assignments of respective peaks in NMR (Nuclear Magnetic Resonance Spectroscopy) are as below.

$^1$H NMR (400 MHz, DMSO-d6): δ 3.27 (s, 6H, —COOCH$_3$), 3.72 (dd, 2H, J=7.4, 10.2 Hz, —CH—COOCH$_3$), 4.11 (dd, 2H, 7.4 Hz, 10.1 Hz, —CH—C$_6$H$_4$), 5.00 (s, 4H, —NH$_2$—C$_6$H$_4$), 6.51 (d, 4H, 8.4 Hz, NH$_2$—C—CH—), 6.95 (d, 4H, 8.4 Hz, NH$_2$—C—CH—CH—)

Synthesis of N,N'-diacetyl (4,4'-diaminotruxillate)

The synthetic pathway of N,N'-diacetyl (4,4'-diaminotruxillate) according to the present invention is shown in the following reaction Formula 14.

[Formula 14]

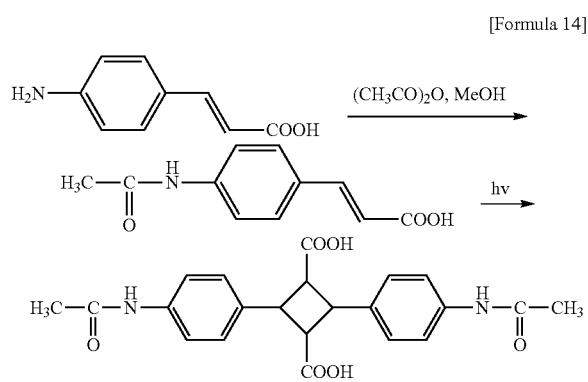

N,N'-diacetyl (4,4'-diaminotruxillate) (DNAc-DATXA) according to the to present invention can be obtained by the synthesis shown in the reaction Formula 14. First, the 4-amino cinnamic acid (4-ACA) (10.0 g, 61.3 mmol) and methanol (180 ml) were added to a flask, to which acetic anhydride (20 ml, 212 mmol) was added, and stirred at room temperature for a day. The product was filtrated, washed with methanol and dried (10.3 g, 81.7%). The obtained 4-acetoaminocinnamic acid (1.00 g, 4.87 mmol) and hexane (50 ml) were added to a flask, and irradiated with UV (λ=250-450 nm). It was filtrated and dried to obtain N,N'-diacetyl (4,4'-diaminotruxillate) (DNAc-DATXA) (0.93 g, 93.0%).

Figure 2:
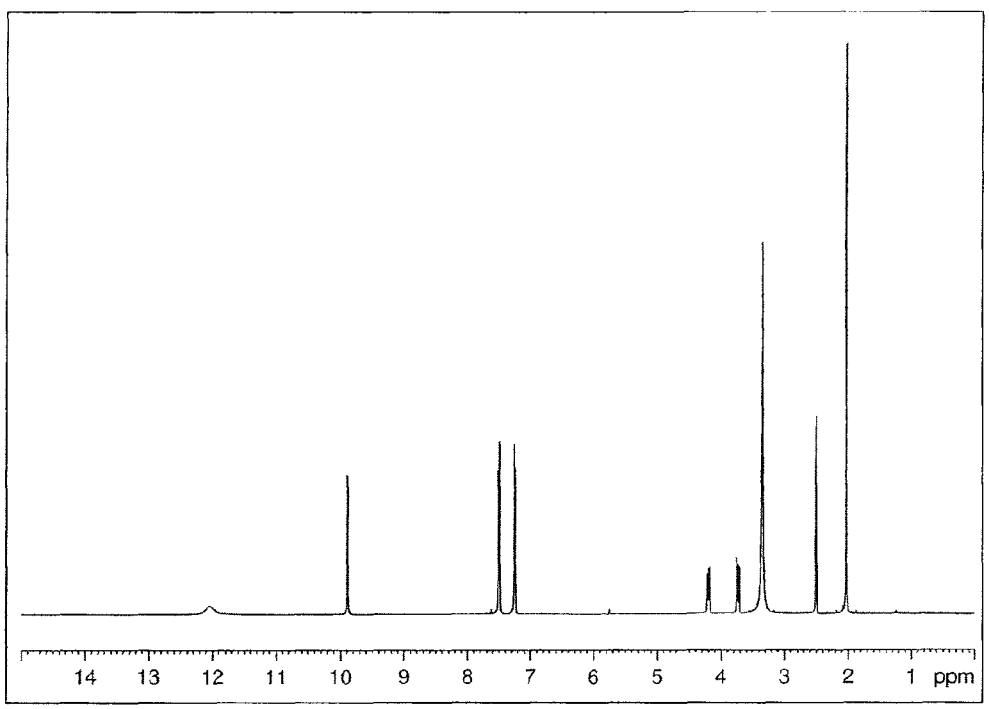
FIG. 2 is NMR spectrum of N,N'-diacetyl (4,4'-diaminotruxillate) (DNAc-DATXA) according to the present invention.

NMR spectrum of the obtained N,N'-diacetyl (4,4'-diaminotruxillate) (DNAc-DATXA) is shown in FIG. 2. Assignments of respective peaks in NMR are as below.

$^1$H NMR (400 MHz, DMSO-d6): δ 2.03 (s, 6H, —NHCOCH$_3$), 3.73 (dd, 2H, J=7.4, 10.2 Hz, —CH—COOH), 4.20 (dd, 2H, J=7.4, 10.2 Hz, —CH—C$_6$H$_4$—), 7.25 (d, 4H, J=8.5 Hz, CH$_3$CONH—C—CH—CH—), 7.50 (d, 4H, J=8.5 Hz, CH$_3$CONH—C—CH—), 9.89 (s, 2H, CH$_3$CONH—), 12.04 (s, 2H, —COOH, 1H)

Exemplary synthesis of polyimide

The synthetic pathway of polyamide acid (PAA) according to the present invention is shown in the following reaction Formula 15.

[Formula 15]

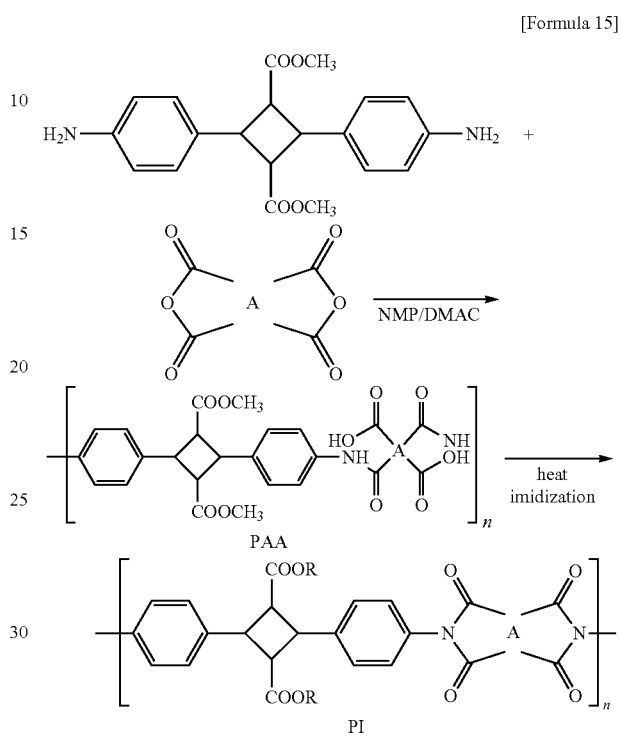

The polyamide acid (PAA) according to the present invention can be obtained by the synthesis shown in reaction Formula 15. First, 2,4-bis(4-aminophenyl)-1,3-dialkyl cyclobutanedicarboxylate (DATXA-DM) (0.20 g, [0.5647 mmol]) was dissolved in N-methyl-2-pyrrolidinone (NMP) ([0.5647 mL], [1M]) in a 10 mL test tube, and stirred by a mechanical stirrer under a nitrogen atmosphere.

Subsequently, when cyclobutanetetracarboxylic acid dianhydride (CBDA) (0.11 g, [0.5647 mmol]) was added, the solution turned pale yellow. The reaction solution was vigorously stirred at room temperature for 24 hours, resulting in a viscous solution. When the solution was diluted with NMP (N-methylpyrrolidone) and dripped into water, fibrous solids were precipitated. The solids were collected by filtration, thoroughly washed with water, and then vacuum-dried in a desiccator. The solids were dissolved in NMP again, and a resulting yellow solution was cast on a silicon wafer to obtain a film. As results of structures analysis of the obtained film by FT-IR (Fourier transform infrared spectroscopy) and NMR (Nuclear Magnetic Resonance Spectroscopy) revealed that the film was composed of the target polyamide acid (PAA-1). The yield was 85 wt %.

A polyimide film (PI-1) was obtained by gradually heating the polyamide acid film (PAA-1) at 100° C., 150° C., 200° C. and 250° C. in an oven (for one hour at each temperature). The imidization was confirmed by FT-IR.

Figure 3:
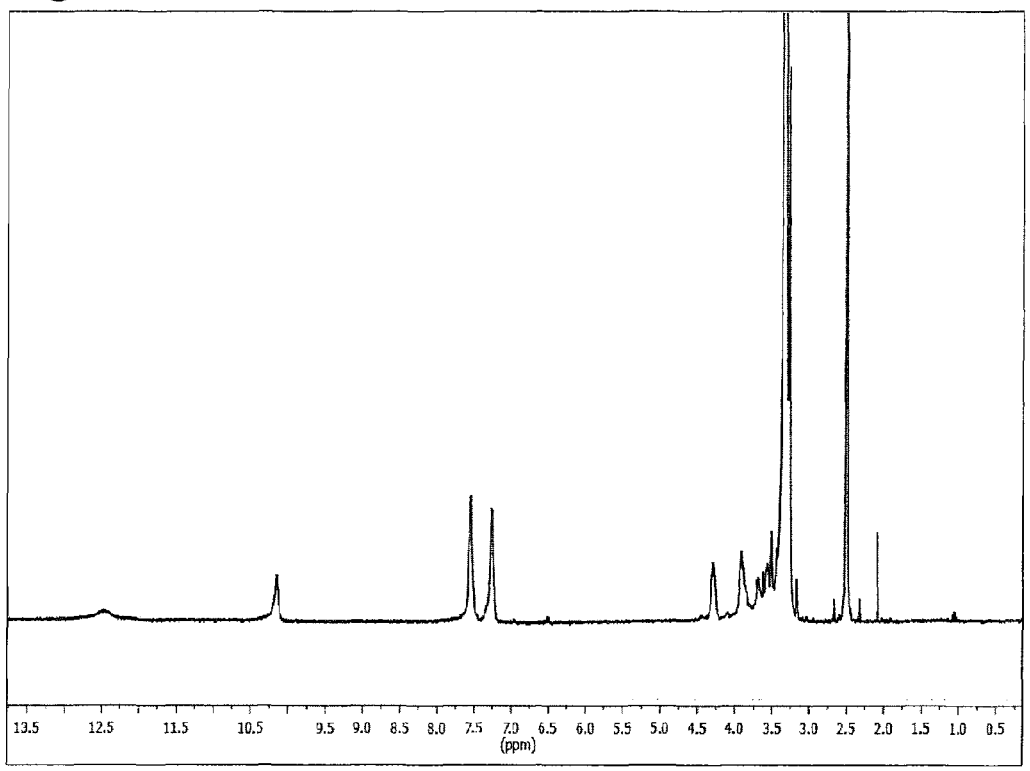
FIG. 3 is NMR spectrum of polyamide acid (PAA-1) according to the present invention.
Figure 4:
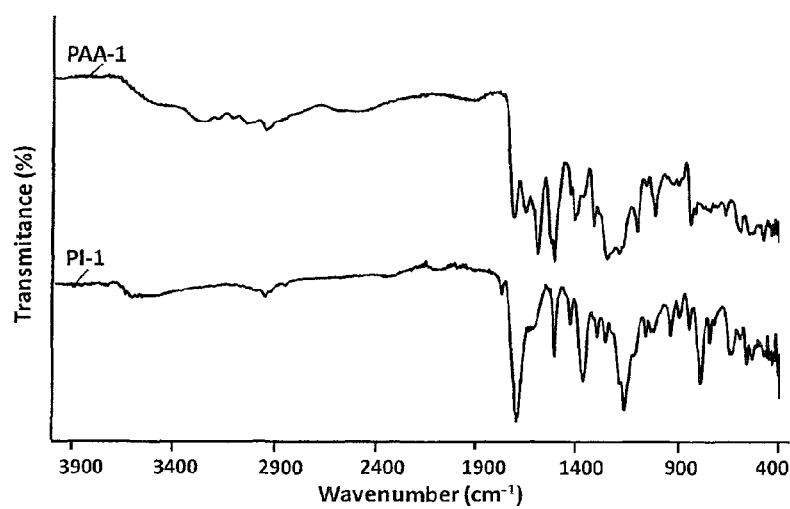
FIG. 4 is FT-IR spectrum of polyamide acid (PAA-1) and polyimide (PI-1) according to the present invention.
Figure 5:
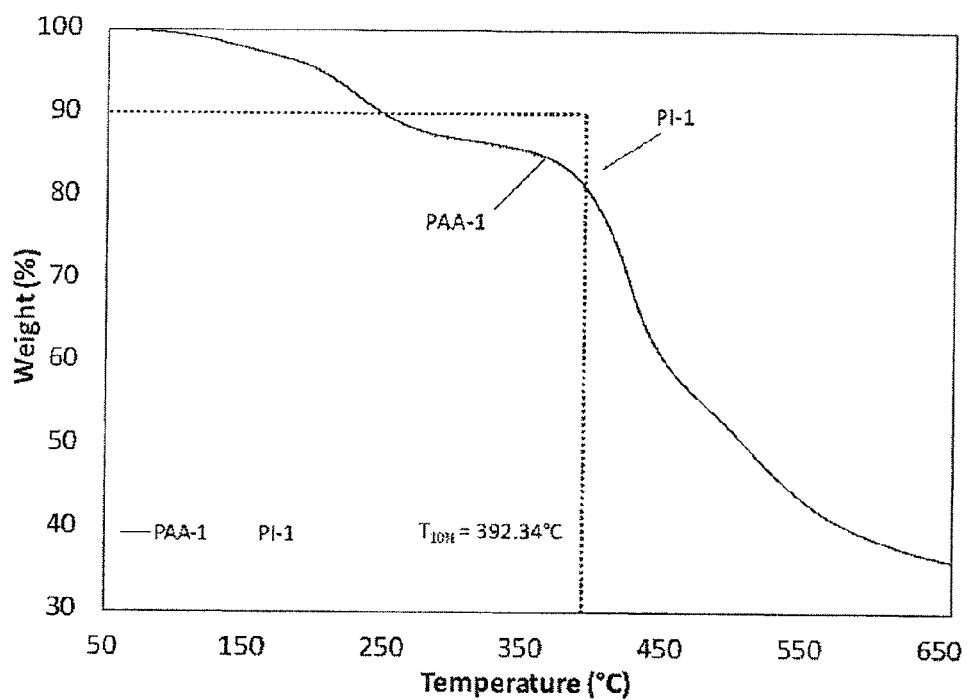
FIG. 5 is TGA curves of polyamide acid (PAA-1) and polyimide (PI-1) according to the present invention.

NMR spectrum of the obtained polyamide acid (PAA-1) is shown in FIG. 3. In addition, FT-IR spectrum of polyamide acid (PAA-1) and polyimide (PI-1) are shown in FIG. 4. Furthermore, TGA curves in the analysis of the obtained polyamide acid (PAA-1) and polyimide (PI-1) by TGA (thermogravimetric analysis) is shown in FIG. 5. These TGA curves show that a heat-resistant temperature (10% decomposition temperature) of the polyimide (PI-1) was 392° C.

Polymerization was carried out by the same method using pyromellitic acid instead of CBDA. An amount of the used NMP was (0.9412 mL, [0.6 M]), and methanol was used instead of water in reprecipitation. The yield was 80 wt %. As results of structures analysis of the obtained film by FT-IR and NMR revealed that the film was composed of the target polyamide acid (PAA-2).

Figure 6:
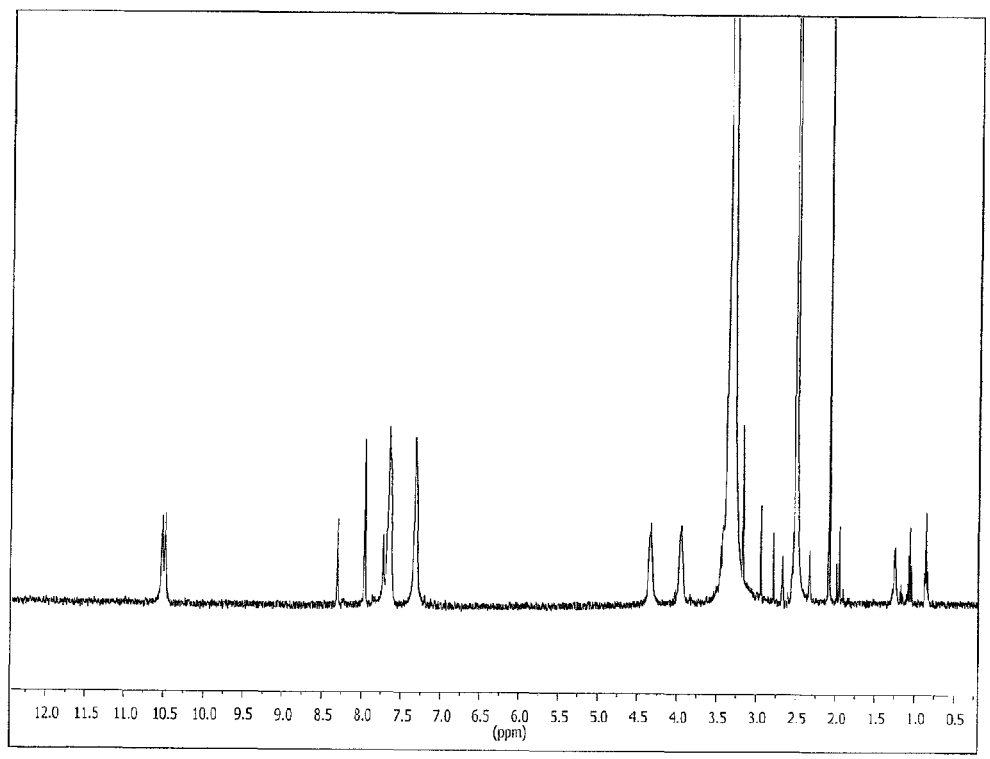
FIG. 6 is NMR spectrum of polyamide acid (PAA-2) according to the present invention.
Figure 7:
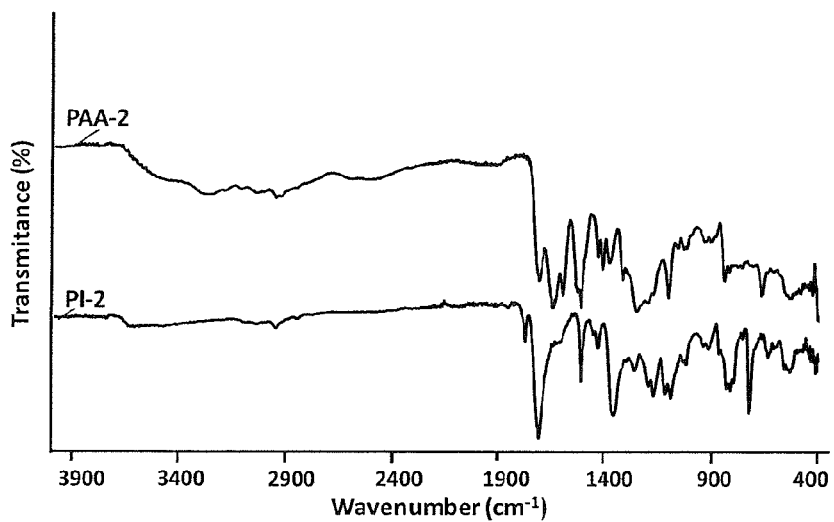
FIG. 7 is FT-IR spectrum of polyamide acid (PAA-2) and polyimide (PI-2) according to the present invention.
Figure 8:
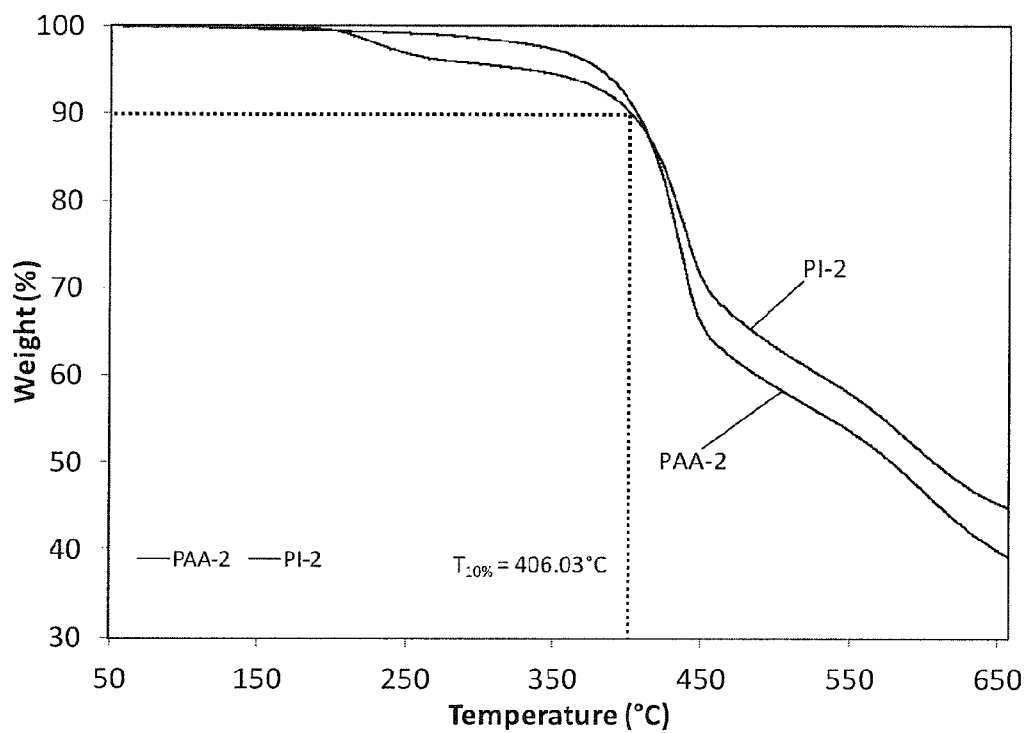
FIG. 8 is TGA curves of polyamide acid (PAA-2) and polyimide (PI-2) according to the present invention.

NMR spectrum of the obtained polyamide acid (PAA-2) is shown in FIG. 6. In addition, FT-1R spectrum of polyamide acid (PAA-2) and polyimide (PI-2) are shown in FIG. 7. Furthermore, TGA curves of the resulting polyamide acid (PAA-2) and polyimide (PI-2) are shown in FIG. 8. These TGA curves show that a heat-resistant temperature (10% decomposition temperature) of the polyimide (PI-2) was 406 deg C.

In addition, molecular weights of respective polyamide acids ware measured by GPC (Gel permeation Chromatography) (Concentration of the sample: 0.5 mg mL-1, Solvent: dimethylformamide, External standard: pullulan). The results are shown in the following Table 1. In Table 1, Mw refers to weight-average molecular weight, Mn refers to number-average molecular weight and PDI refers to polydispersity. PDI is a value obtained by dividing Mw by Mn.

TABLE 1

| Polymer | $M_n$ (g/mol) | $M_w$ (g/mol) | PDI |
| --- | --- | --- | --- |
| PAA-1 | $4.17 \times 10^4$ | $5.39 \times 10^4$ | 1.29 |
| PAA-2 | $4.52 \times 10^4$ | $5.79 \times 10^4$ | 1.28 |

Exemplary Synthesis of Aliphatic Polyamide

The synthetic pathway of aliphatic polyamide according to the present invention is shown in the following reaction Formula 16.

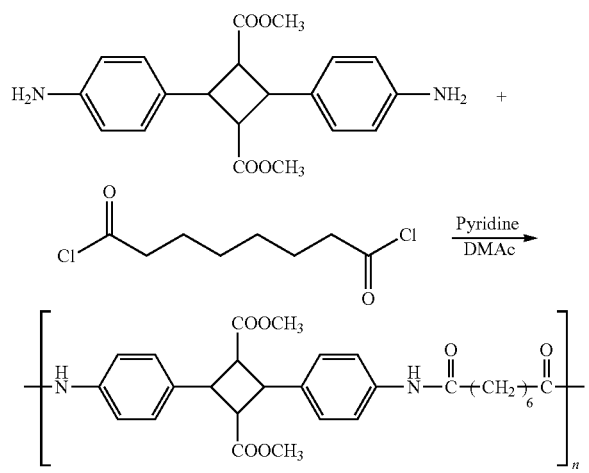

[Formula 16]

The aliphatic polyamide according to the present invention can be obtained by the synthesis shown in reaction Formula 16. First, dimethyl 4,4'-diaminotruxillate (300.9 mg, 0.85 mmol), dehydrated DMAc (0.85 ml), dehydrated pyridine (0.17 ml) and suberoyl chloride (0.16 ml, 0.86 mmol) were added to a nitrogen-substituted flask, and stirred at room temperature for three hours. To the reactant, NMP (2.5 ml) was added and uniformed, then dripped into 60 ml of methanol and re-precipitated to obtain a white fibrous polymer. The obtained polymer was dissolved in a small amount of DMF (Dimethylformamide), dripped onto a silicon wafer, and then heated to produce a film.

Figure 9:
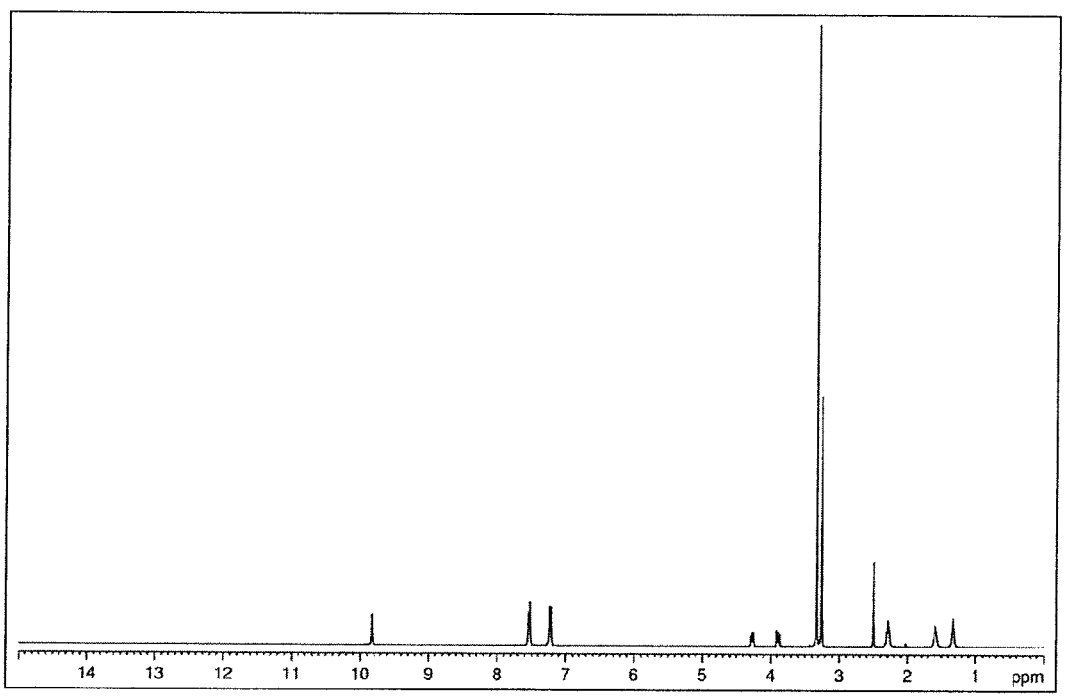
FIG. 9 is NMR spectrum of aliphatic polyamide according to the present invention.

Measurement of the molecular weight of the obtained aliphatic polyamide film by GPC showed number-average molecular weight=$7.25 \times 10^3$, weight-average molecular weight=$7.99 \times 10^3$ and dispersity=1.10 (pullulan conversion). NMR spectrum is as shown in FIG. 9. Assignments of respective peaks are as below.

$^1$H NMR (400 MHz, DMSO-d6): δ 1.33 (4H, —NHCH$_2$CH$_2$CH$_2$—), 1.59 (4H, —NHCH$_2$CH$_2$CH$_2$—), 2.29 (4H, —NHCH$_2$CH$_2$CH$_2$—), 3.26 (6H, —COOCH$_3$), 3.88 (2H, CH—COOCH$_3$), 4.27 (2H, CH—C$_6$H$_4$—), 7.21-7.54 (8H, arom), 9.84 (2H, —C$_6$H$_4$—NH—CO—)

Figure 10:
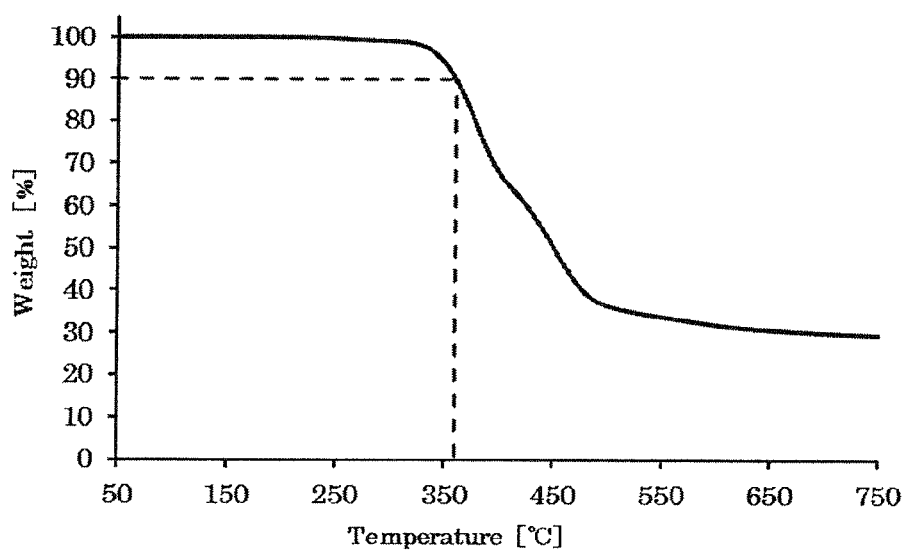
FIG. 10 is TGA curve of aliphatic polyamide according to the present invention.

TGA curve of the obtained aliphatic polyamide film is shown in FIG. 10. The measuring range was 50-750 deg C., the rate of temperature rise was 10° C./min., and the heat-resistant temperature (10% weight reduction temperature) of the aliphatic polyamide film was 360 deg C.

Exemplary Synthesis of Aromatic Polyamide

The synthetic pathway of aromatic polyamide according to the present invention is shown in the following reaction Formula 17.

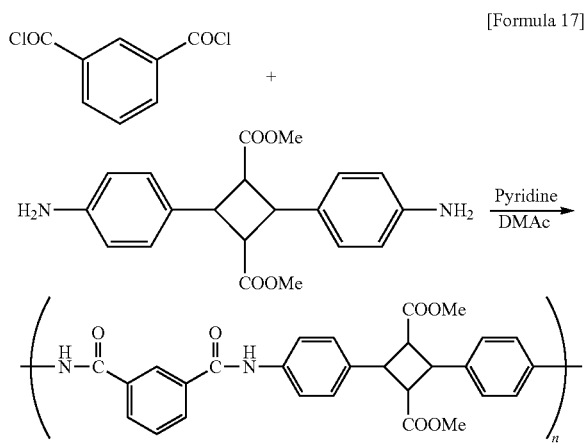

[Formula 17]

The aromatic polyamide according to the present invention can be obtained by synthesis shown in the reaction Formula 17. First, a dehydrated pyridine and a dehydrated DMAc (0.3 ml) were added to a nitrogen-substituted test tube containing isophthalic acid dichloride (60 mg, 0.3 mmol) and DATXA-DM (100 mg, 0.3 mmol) and stirred at room temperature for 12 hours. DMAc (2 ml) was added to the reactant, and the solution was uniformed, then dripped into methanol (40 ml) to re-precipitate the polymer. The precipitated white solids were collected and vacuum-dried for 5 hours to obtain a white polymer (120 mg, yield: 82%). The white polymer was dissolved in a small amount of DMF, dripped onto a silicon wafer, and dried on a hot plate to produce a film.

Figure 11:
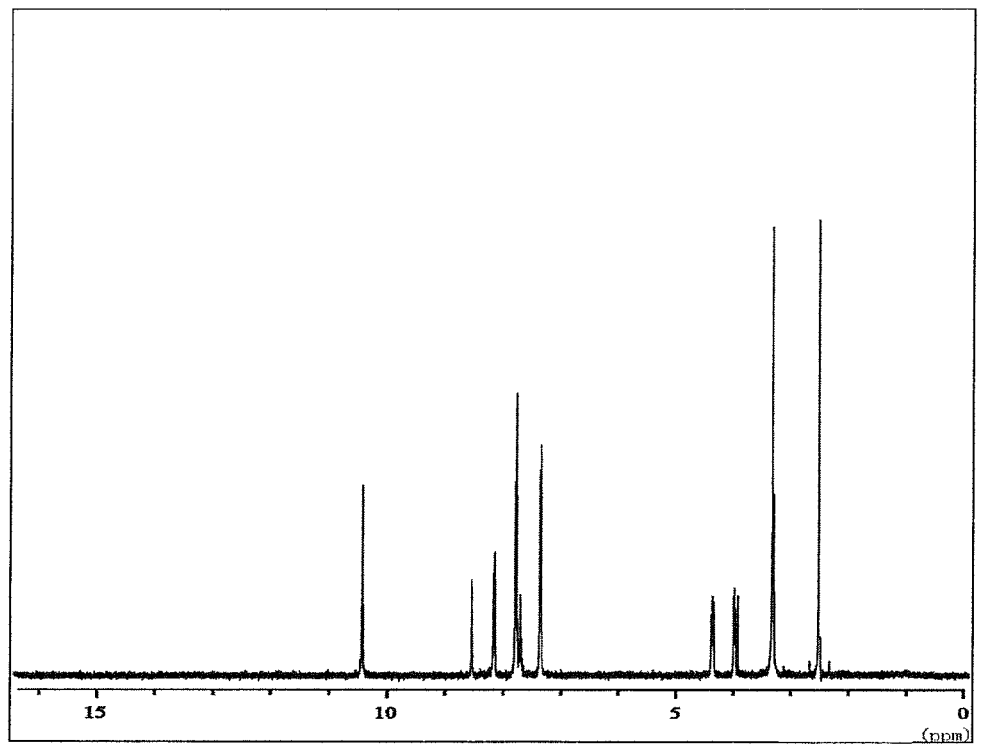
FIG. 11 is NMR spectrum of aromatic polyamide according to the present invention.

Measurement of the molecular weight of the obtained aromatic polyamide film by GPC showed number-average molecular weight=$8.0 \times 10^4$, weight-average molecular weight=$8.9 \times 10^4$ and dispersity=1.26 (pullulan conversion). NMR spectrum is as shown in FIG. 11. Assignments of respective peaks are as below.

$^1$H NMR (400 MHz, DMSO-d6): δ 3.25 (6H, —COOCH$_3$), 3.96-4.00 (2H, —CHCOOH—), 4.34-4.39 (2H, —CHC$_6$H$_4$—), 7.34-8.54 (12H, arom.), 10.42 (2H, —C$_6$H$_4$—NH—CO—)

Figure 12:
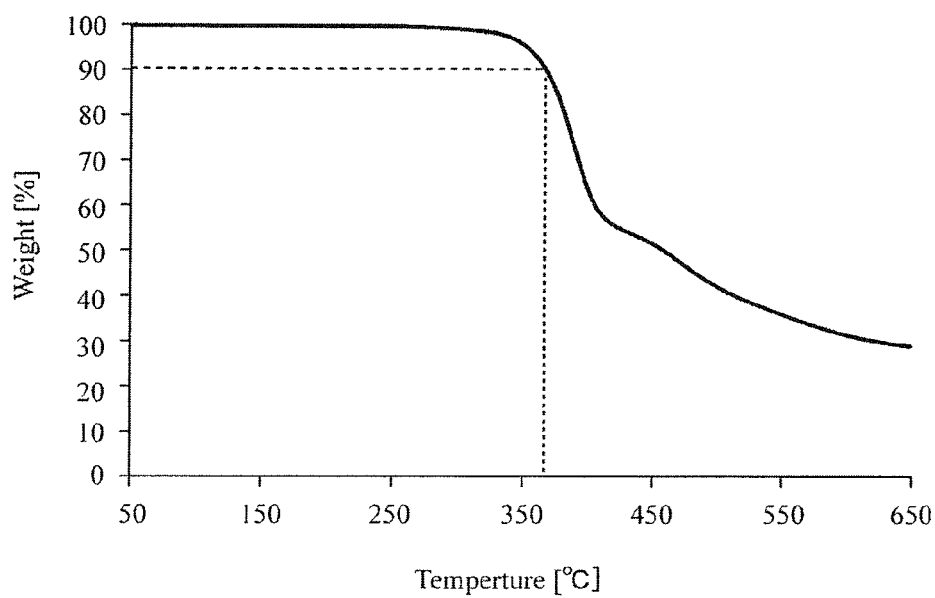
FIG. 12 is TGA curve of aromatic polyamide according to the present invention.

TGA curve of the obtained aromatic polyamide film is shown in FIG. 12. The measuring range was 50-650 deg C., the rate of temperature rise was 10 deg C./min., and the heat-resistant temperature (10% weight reduction temperature) of the aromatic polyamide film was 366 deg C.

Exemplary Synthesis of Polyamide using N,N'-diacetyl (4,4'-diaminotruxillate) (DNAc-DATXA)

The synthetic pathway of the polyamide using N,N'-diacetyl (4,4'-diaminotruxillate) (DNAc-DATXA) according to the present invention is shown in the following reaction Formula 18.

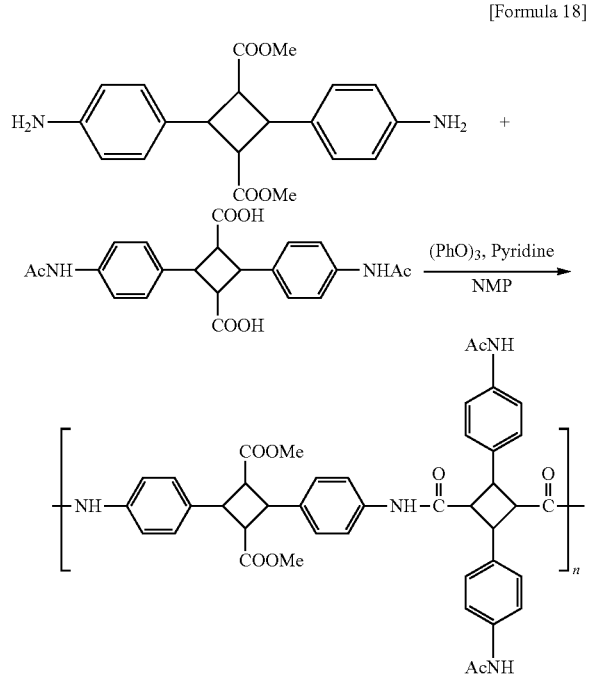

[Formula 18]

The polyamide using N,N'-diacetyl (4,4'-diaminotruxillate) (DNAc-DATXA) according to the present invention can be obtained by the synthesis shown in the reaction Formula 18. First, DATXA-DM (86.3 mg, 0.24 mmol), DNAc-DATXA (99.5 mg, 0.24 mmol) and dehydrated NMP (0.24 ml) are added to a nitrogen-substituted flask. Furthermore, triphenyl phosphite (70 µl, 0.27 mmol) and pyridine (120 µl, 1.49 mmol) were dripped, and stirred at 100° C. for 1 hour. NMP (2 ml) was added to the reactant, and the solution was uniformed, then dripped into methanol (60 ml) to re-precipitate the polymer. The precipitated fibrous substance was collected, and dried at 200 deg C. for 1 hour to obtain a white fibrous polymer (150.1 mg, yield: 89.6%). The fibrous polymer was dissolved in a small amount of DMF, dripped onto a silicon wafer, and dried at 120 deg C. for 1 hour to produce a film.

Measurement of the molecular weight of the obtained polyamide film by GPC showed number-average molecular weight=1.02×10$^4$, weight-average molecular weight=2.10×10$^4$ and dispersity=2.06 (pullulan conversion). Assignments of respective peaks in NMR spectrum are as below.

1H NMR (400 MHz, DMSO-d6): δ 1.95 (6H, NHCOCH$_3$), 3.13 (6H, COOCH$_3$), 3.79-4.36 (8H, cyclobutane), 7.00-7.49 (16H, arom.), 9.71-9.93 (4H, NH)

Figure 13:
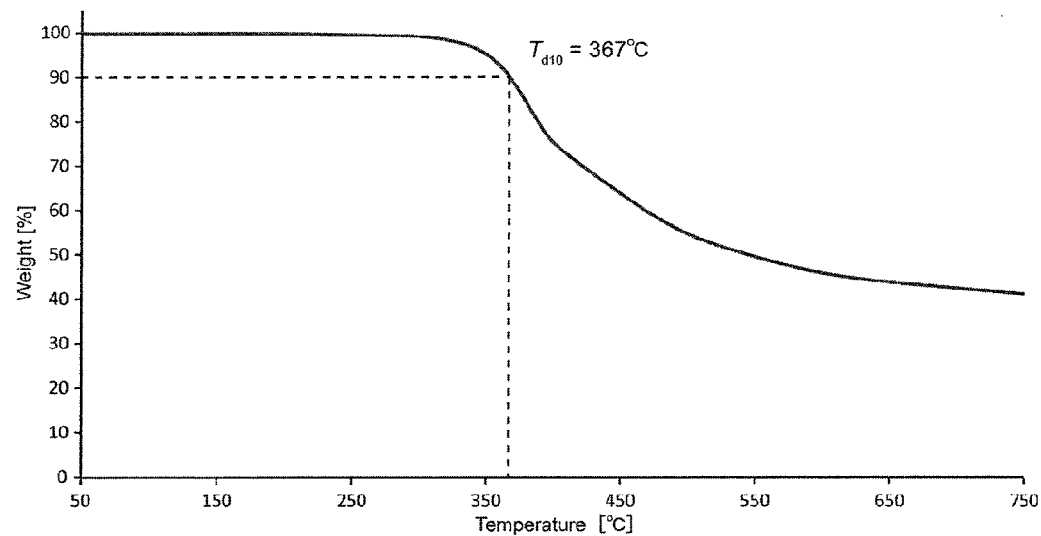
FIG. 13 is TGA curve of polyamide synthesized by using N,N'-diacetyl (4,4'-diaminotruxillate) (DNAc-DATXA) according to the present invention.

TGA curve of the obtained polyamide film is shown in FIG. 13. The measuring range was 50-750° C., the rate of temperature rise was 10 deg C./min., and the heat-resistant temperature (10% weight reduction temperature) of the polyamide film was 367° C.

Exemplary Synthesis of Aliphatic Polyurea

The synthetic pathway of aliphatic polyurea according to the present invention is shown in the following reaction Formula 19.

[Formula 19]

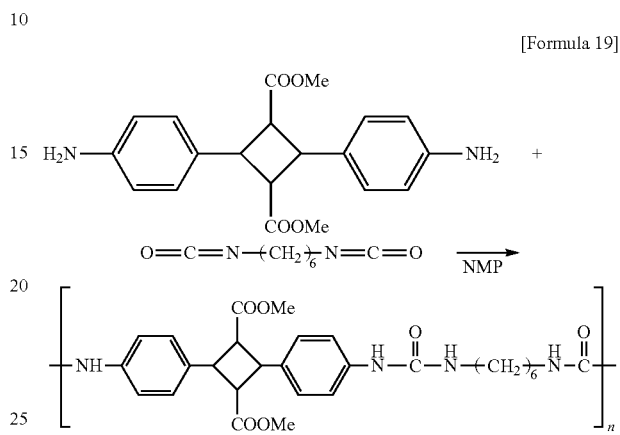

The aliphatic polyurea according to the present invention can be obtained by the synthesis shown in the reaction Formula 19. First, DATXA-DM (100.8 mg, 0.28 m mol), hexamethylenediisocyanate (47.5 mg, 0.28 mmol), and dehydrated NMP (0.28 ml) are added to a nitrogen-substituted flask, stirred at room temperature for 12 hours and then at 100° C. for 1 hour. NMP (1 ml) was added to the reactant, and the solution was uniformed, then dripped into methanol (40 ml) to re-precipitate the polymer. The precipitated fibrous substance was collected, and dried at 200° C. for 1 hour to obtain a white fibrous polymer (126.3 mg, yield: 85.2%). The fibrous polymer was dissolved in a small amount of DMF, dripped onto a silicon wafer, and dried at 120° C. for 1 hour to produce a film.

Figure 14:
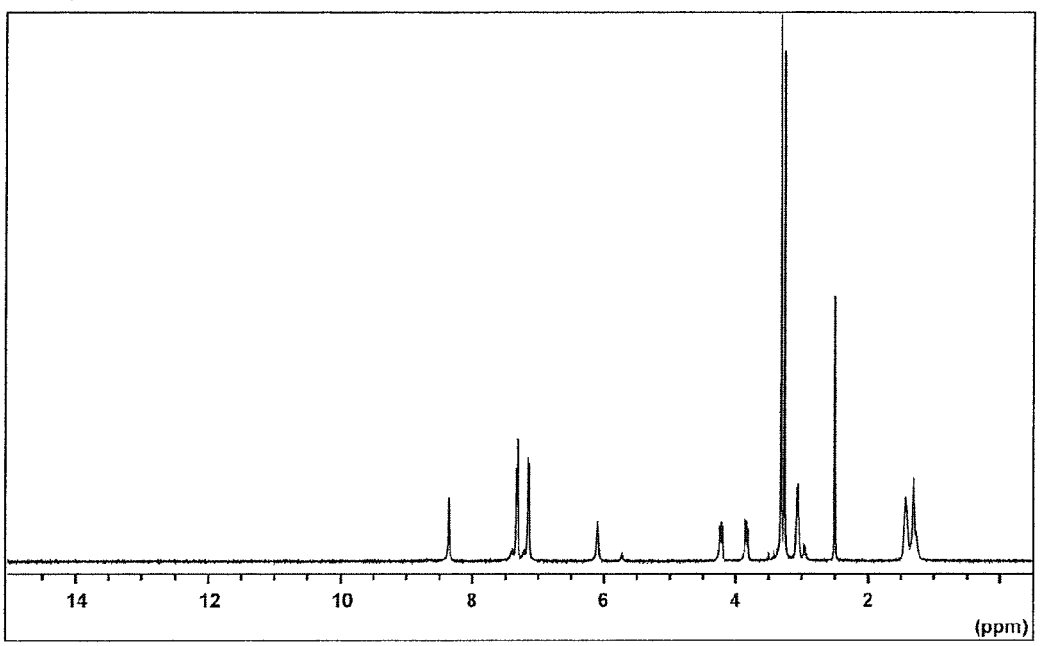
FIG. 14 is NMR spectrum of aliphatic polyurea according to the present invention.

Measurement of the molecular weight of the obtained aliphatic polyurea film by GPC showed number-average molecular weight=1.39×10$^4$, weight-average molecular weight=3.37×10$^4$ and dispersity=2.42 (pullulan conversion). NMR spectrum is as shown in FIG. 14. Assignments of respective peaks are as below.

$^1$H NMR (400 MHz, DMSO-d6): δ 1.29 (4H, —NHCH$_2$CH$_2$CH$_2$—), 1.42 (4H, —NHCH$_2$CH$_2$CH$_2$—), 3.06 (4H, —NHCH$_2$CH$_2$CH$_2$—), 3.25 (6H, —COOCH$_3$), 3.83 (2H, CH—COOCH$_3$), 4.21 (2H, CH—C$_6$H$_4$—), 6.09 (2H, CONH—C$_6$H$_{12}$—), 7.14-7.31 (8H, arom.), 8.35 (2H, —C$_6$H$_4$—NH—CO—)

Figure 15:
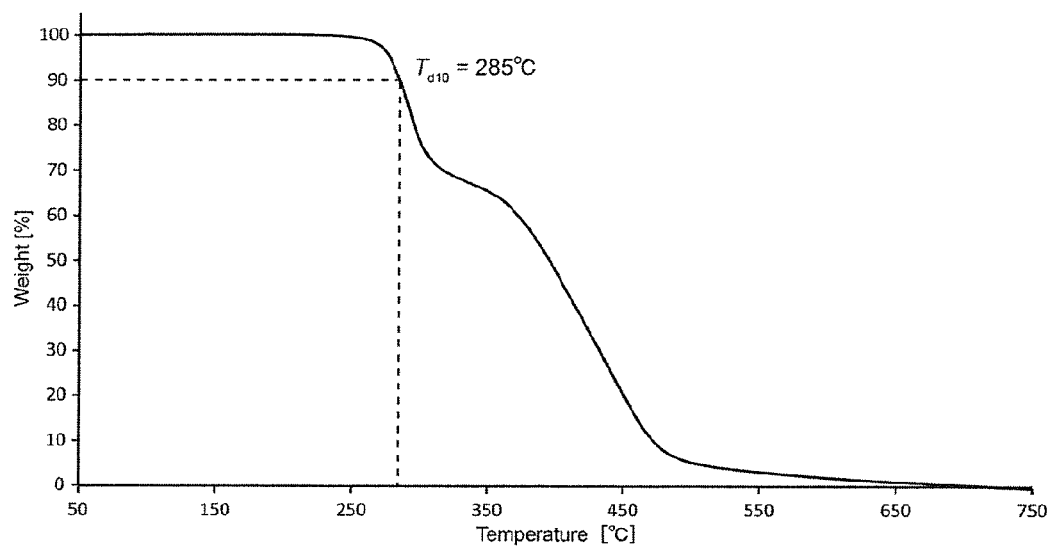
FIG. 15 is TGA curve of aliphatic polyurea according to the present invention.

TGA curve of the obtained aliphatic polyurea film is shown in FIG. 15. The measuring range was 50-750 deg C., the rate of temperature rise was 10 deg C./min., and the heat-resistant temperature (10% weight reduction temperature) of the polyurea film was 285 deg C.

Exemplary Synthesis of Aromatic Polyurea

The synthetic pathway of aromatic polyurea according to the present invention is shown in the following reaction Formula 20.

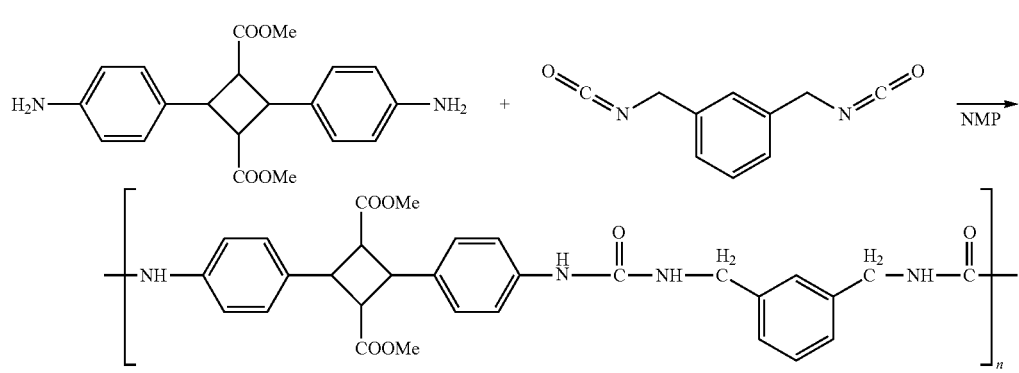

[Formula 20]

The aliphatic aromatic according to the present invention can be obtained by the synthesis shown in the reaction Formula 20. First, DATXA-DM (101.0 mg, 0.28 m mol), m-xylilenediisocyanate (47.5 mg, 0.28 mmol), and dehydrated NMP (0.28 ml) are added to a nitrogen-substituted flask, stirred at room temperature for 12 hours and then at 100 deg C. for 1 hour. NMP (1 ml) was added to the reactant, and the solution was uniformed, then dripped into methanol (40 ml) to re-precipitate the polymer. The precipitated solid body was collected, and dried at 200 deg C. for 1 hour to obtain a white powder of a polymer (140.0 mg, yield: 94.0%). The polymer was dissolved in a small amount of DMF, dripped onto a silicon wafer, and dried at 120 deg C. for 1 hour to produce a film.

Measurement of the molecular weight of the obtained aromatic polyurea film by GPC showed number-average molecular weight=$1.13\times10^4$, weight-average molecular weight=$3.05\times10^4$ and dispersity=2.69 (pullulan conversion). Assignments of respective peaks in NMR spectrum are as below.

1H NMR (400 MHz, DMSO-d6): δ 3.25 (6H, COOCH$_3$), 3.84 (2H, CH—COOCH$_3$), 4.22 (2H, CH—C$_6$H$_4$), 4.28 (4H, NH—CH$_2$—), 6.58 (2H, CONHCH$_2$), 7.08-7.43 (12H, arom.), 8.52 (2H, C$_6$H$_4$NHCO)

Figure 16:
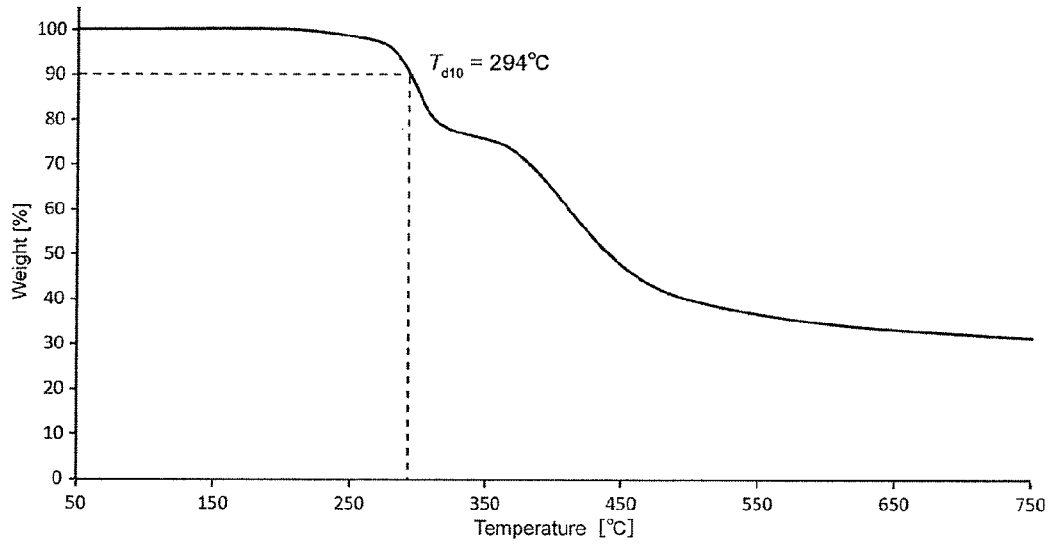
FIG. 16 is NMR spectrum of aromatic polyurea according to the present invention.

TGA curve of the obtained aromatic polyurea film is shown in FIG. 16. The measuring range was 50-750 deg C., the rate of temperature rise was 10 deg C./min., and the heat-resistant temperature (10% weight reduction temperature) of the polyurea film was 294 deg C.

Comparison of Properties

Figure 17:
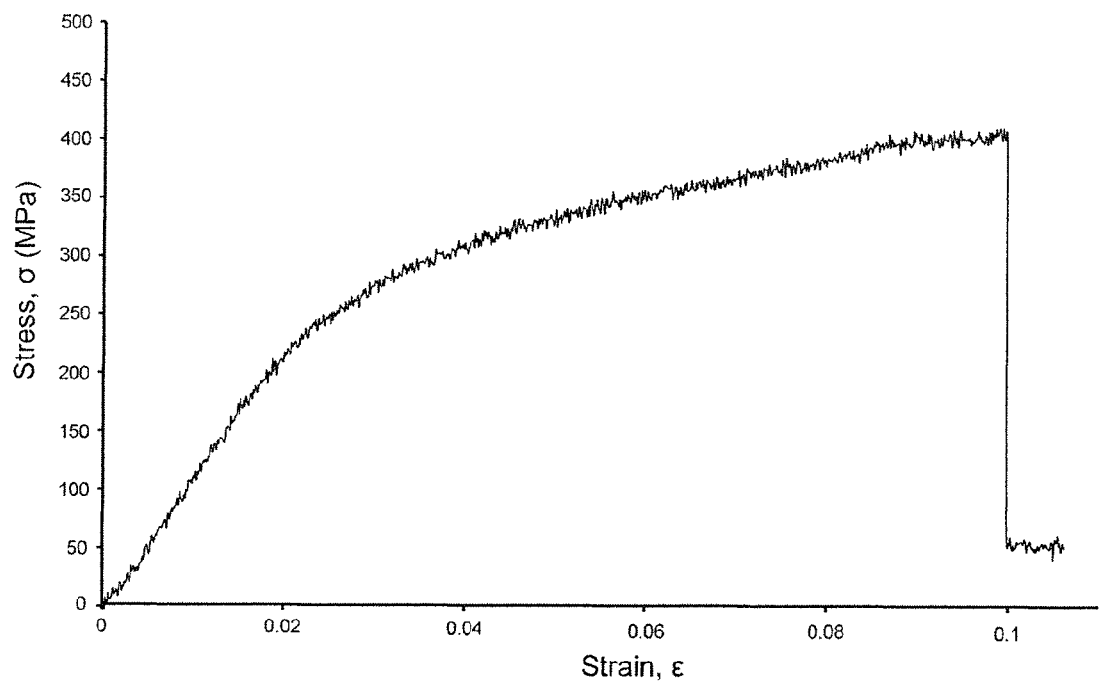
FIG. 17 is a graph showing the results of the tensile strength test for aromatic polyamide.

Hereinafter, various test measurements were carried out for the polyamide using N,N'-diacetyl(4,4'-diaminotruxillate) (DNAc-DATXA) of Examples of the present invention. In addition, the results were compared with those of various test measurements for known polymer materials. The results are shown in Table 2. In Table 2, Mw refers to weight-average molecular weight, Mn refers to number-average molecular weight and PDI refers to polydispersity. PDI is a value obtained by dividing Mw by Mn. In addition, the results of the tensile strength test for the polyamide of Examples of the present invention are shown in FIG. 17

TABLE 2

| | material | Mn (g/mol) | Mw (g/mol) | PDI | $T_{d10}$ (° C.) | $T_g$ (° C.) | Modulus, $E_{init}$ (GPa) | Stress, σ (MPa) |
|---|---|---|---|---|---|---|---|---|
| Invention | poly(DATXA-DM-co-DNAc-DATXA) | $1.0 \times 10^4$ | $2.1 \times 10^4$ | 2.06 | 367 | 273 | 11.6 | 407 |
| current | Kapton ® | — | — | — | — | — | 0.7 | 120 |
| | polyamide 11 | $2.5 \times 10^4$ | $6.5 \times 10^4$ | 2.60 | — | 29 | — | — |
| | polyamide 11 | — | — | — | — | — | 0.61 | — |
| | polyamide 11 | — | — | — | — | 45 | 1.3 | 67 |
| | collagen | — | — | — | — | — | 1.2 | 120 |
| | elastin | — | — | — | — | — | 0.0011 | 2 |
| | keratin | — | — | — | — | — | 2.5 | — |
| | titin | — | — | — | — | — | 0.002 | — |
| | Araneus viscid silk | — | — | — | — | — | 0.003 | 500 |

Among the known polymer materials shown in Table 2, Kapton (R) is a polyimide derived from petroleum. Polyamide 11 is a naturally-derived polyamide. Collagen, elastin, keratin, titin and Araneus viscid silk are organism-derived proteins, each of which is a type of polyamides.

As shown in Table 2, in the polyamide using N,N'-diacetyl (4,4'-diaminotruxillate) (DNAc-DATXA) of Examples of the present invention, the heat-resistant temperature (10% weight reduction temperature) Td10 is 367° C., the glassy-transition temperature Tg is 273° C., showing an extremely-higher heat resistance than of conventional articles. In addition, the Young's modulus $E_{int}$ is 11.6 GPa and the breaking stress σ is 407 MPa, showing an extremely-higher stress than of conventional articles.

Recyclability

In relation to the polyamide using N,N'-diacetyl(4,4'-diaminotruxillate) (DNAc-DATXA) of Examples of the present invention, the decomposition pathway for restoration to the polymer raw material is shown in the following reaction Formula 21.

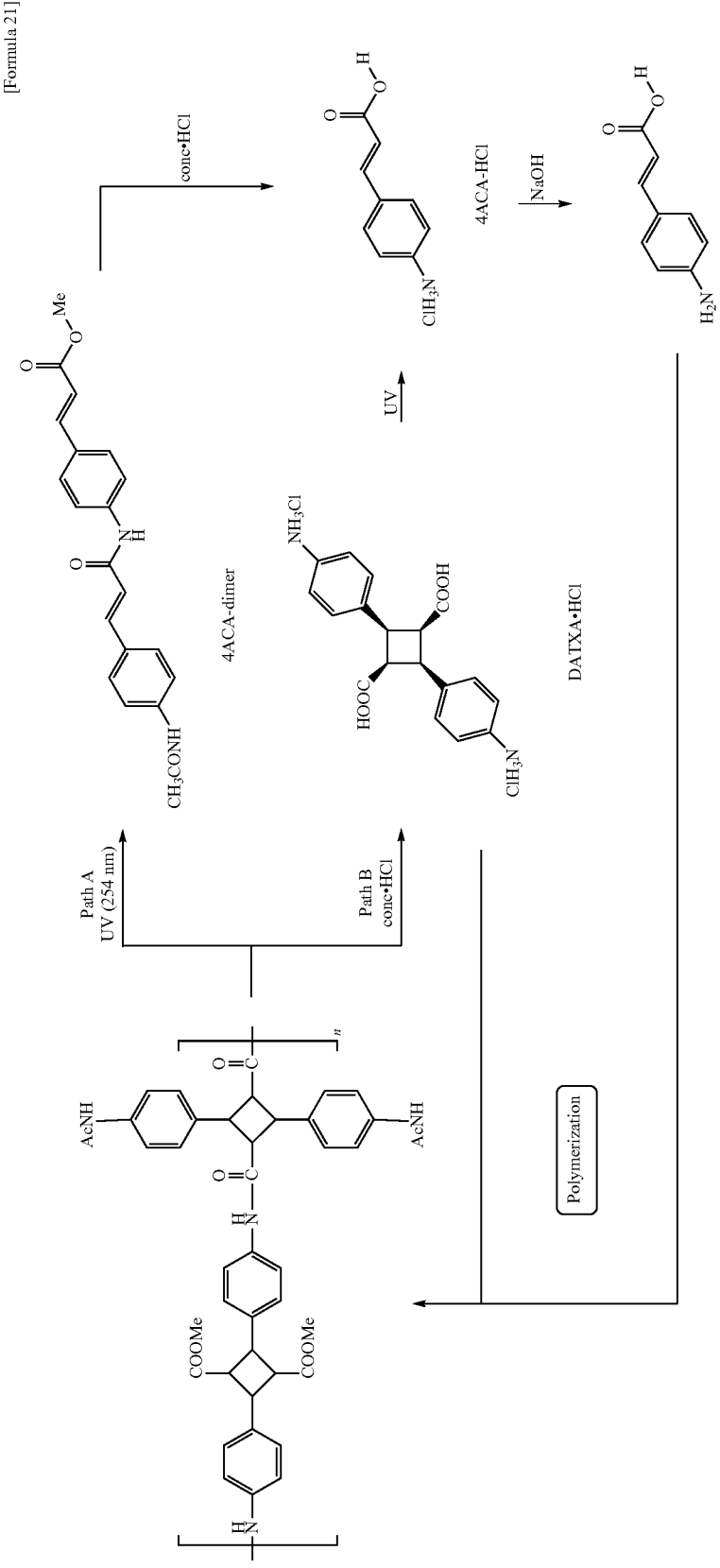
[Formula 21]

The polyamide according to the present invention can be restored to the polymer raw material by the decomposition pathway shown in the reaction Formula 21. That is, in Path A, the polyamide is converted to 4ACA-dimer by irradiation with ultraviolet ray (wavelength: 254 mu), then restored to 4-amino cinnamic acid (4ACA) by hydrolyzation with hydrochloric acid (HCl) to recycle it as a polymer raw material. In Path B, the polyamide is converted to DATXA-HCl by hydrolyzation with hydrochloric acid (HCl), then restored to 4-amino cinnamic acid (4ACA) by irradiation with ultraviolet ray (wavelength: 254 nm) to recycle it as a polymer raw material. Also, in Path B, the DATXA-HCl through hydrolyzation with hydrochloric acid (HCl) may be recycled as a polymer raw material. Furthermore, in Path A, the 4ACA-dimer through irradiation with ultraviolet ray (wavelength: 254 nm) may be recycled as a polymer raw material.

The invention claimed is:

1. A polymer material, comprising:
a structure represented by Formula 2,

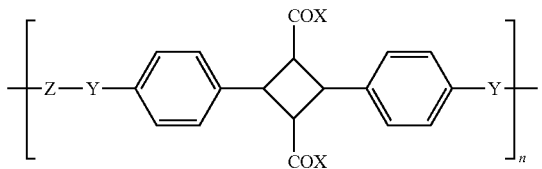

2 where X is —OR, —SR, or —NHR;
R is alkyl group, alkenyl group, or aryl group;
Y is an imide bond, an amide bond, or a urea bond;
Z is an organic link; and
n is a positive integer.

2. The polymer material according to claim 1, wherein the structure represented by Formula 2 has a structure represented by Formula 3,

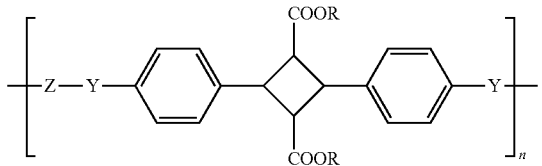

3 where R is alkyl group, alkenyl group, or aryl group;
Y is an imide bond, an amide bond, or a urea bond;
Z is an organic link; and
n is a positive integer.

3. The polymer material according to claim 2, wherein the polymer material is a polyamide having a structure represented by Formula 4,

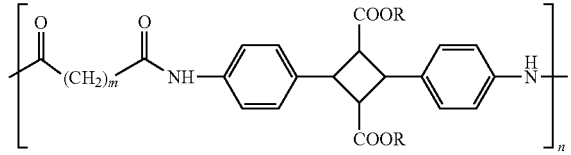

4 where R is alkyl group, alkenyl group, or aryl group;
n is a positive integer; and
m is a positive integer.

4. The polymer material according to claim 2, wherein the polymer material is a polyamide having a structure represented by Formula 5,

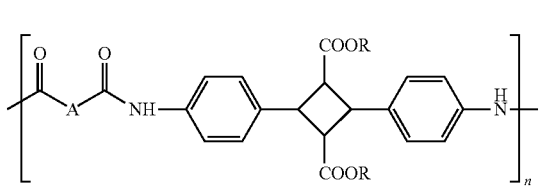

5 where R is alkyl group, alkenyl group, or aryl group;
A represents an aromatic ring or a alicycle; and
n is a positive integer.

5. The polymer material according to claim 2, wherein the polymer material is a polyamic acid having a structure represented by Formula 6,

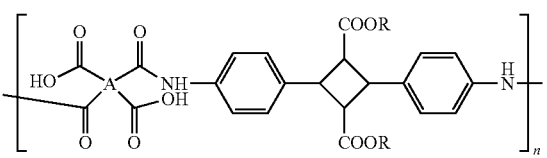

6 where R is alkyl group, alkenyl group, or aryl group;
A represents an aromatic ring or a alicycle; and
n is a positive integer.

6. The polymer material according to claim 2, wherein the polymer material is a polyimide having a structure represented by Formula 7,

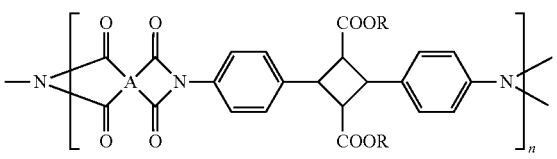

7 where R is alkyl group, alkenyl group, or aryl group;
A represents an aromatic ring or a alicycle; and
n is a positive integer.

7. The polymer material according to claim 2, wherein the polymer material is a polyurea having a structure represented by Formula 8,

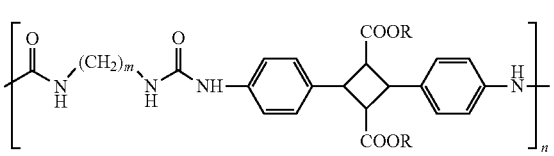

8 where R is alkyl group, alkenyl group, or aryl group;
n is a positive integer; and
m is a positive integer.

8. The polymer material according to claim 2, wherein the polymer material is a polyurea having a structure represented by Formula 9,

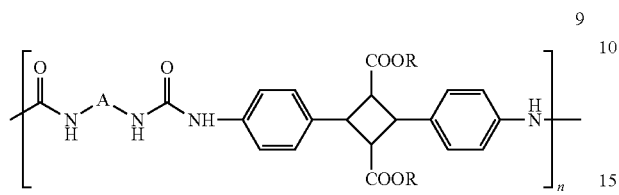

9 where R is alkyl group, alkenyl group, or aryl group;
A represents an aromatic ring or a alicycle; and
n is a positive integer.

9. The polymer material according to claim 2, wherein the polymer material is a polyimide having a structure represented by Formula 10,

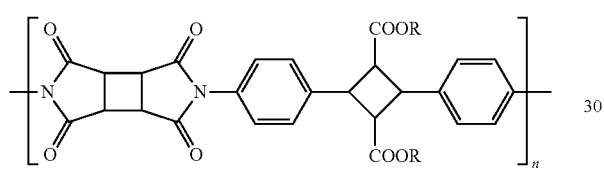

10 where R is alkyl group, alkenyl group, or aryl group; and
n is a positive integer.

10. A manufacturing method of the polymer material according to claim 1, the method comprising:

reacting an amino group in a structure represented by Formula 1,

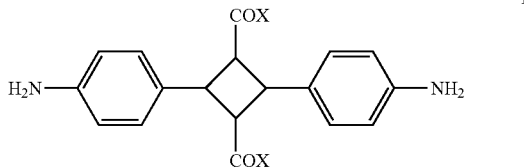

1 where X is —OR, —SR, or —NHR; and
R is alkyl group, alkenyl group, or aryl group,
thereby forming an imide bond, an amide bond, or a urea bond.

11. A recycle method of the polymer material according to claim 1, the method comprising:

irradiating ultraviolet to the polymer material, or hydrolyzing the polymer material with an acid.

* * * * *